US010772767B2

(12) United States Patent
Bjork et al.

(10) Patent No.: US 10,772,767 B2
(45) Date of Patent: Sep. 15, 2020

(54) FIBRIN-COATED WOUND DRESSING

(71) Applicant: 3M INNOVATIVE PROPERTIES COMPANY, St. Paul, MN (US)

(72) Inventors: Jason W. Bjork, Cottage Grove, MN (US); Kurt J. Halverson, Lake Elmo, MN (US); Alexi J. Young, Shoreview, MN (US); Stephanie J. Moeller, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 494 days.

(21) Appl. No.: 14/899,608

(22) PCT Filed: Jun. 12, 2014

(86) PCT No.: PCT/US2014/042040
§ 371 (c)(1),
(2) Date: Dec. 18, 2015

(87) PCT Pub. No.: WO2014/209620
PCT Pub. Date: Dec. 31, 2014

(65) Prior Publication Data
US 2016/0143786 A1  May 26, 2016

Related U.S. Application Data

(60) Provisional application No. 61/840,579, filed on Jun. 28, 2013.

(51) Int. Cl.
*A61F 13/00* (2006.01)
*A61L 15/32* (2006.01)
(Continued)

(52) U.S. Cl.
CPC .. *A61F 13/00063* (2013.01); *A61F 13/00076* (2013.01); *A61F 13/00991* (2013.01);
(Continued)

(58) Field of Classification Search
CPC .......... A61F 13/00063; A61F 13/00991; A61F 13/0206; A61F 13/32
See application file for complete search history.

(56) References Cited

U.S. PATENT DOCUMENTS

| 2,736,721 A | 2/1956 | Dexter |
| RE24,906 E | 12/1960 | Ulrich |

(Continued)

FOREIGN PATENT DOCUMENTS

| IN | 187089 | 1/2002 |
| RU | 2371185 | 10/2009 |

(Continued)

OTHER PUBLICATIONS

Barai, "Improvement of Epidermal Barrier Properties in Cultured Skin Substitutes after Grafting onto Athyic Mice", Skin Pharmacology and Physiology, 2007, vol. 20, pp. 21-28.
(Continued)

*Primary Examiner* — Tatyana Zalukaeva
*Assistant Examiner* — Jessica R Arble
(74) *Attorney, Agent, or Firm* — Qiang Han

(57) ABSTRACT

A fibrin-coated wound dressing article having a flexible film layer, a pressure-sensitive adhesive layer disposed on the flexible film layer, and a fibrin powder layer disposed on a surface of the pressure-sensitive adhesive layer opposite the flexible film layer. Methods of making and using fibrin-coated wound dressing articles are included.

21 Claims, 4 Drawing Sheets

(51) Int. Cl.
    *A61F 13/02*    (2006.01)
    *A61L 15/44*    (2006.01)
    *A61L 15/42*    (2006.01)
    *A61L 15/58*    (2006.01)

(52) U.S. Cl.
    CPC ...... *A61F 13/0206* (2013.01); *A61F 13/0256* (2013.01); *A61F 13/0289* (2013.01); *A61L 15/32* (2013.01); *A61L 15/425* (2013.01); *A61L 15/44* (2013.01); *A61L 15/58* (2013.01); *A61L 2300/412* (2013.01); *A61L 2420/02* (2013.01); *A61L 2420/08* (2013.01)

(56) References Cited

U.S. PATENT DOCUMENTS

| | | | |
|---|---|---|---|
| 3,645,835 | A | 2/1972 | Hodgson |
| 3,723,244 | A | 3/1973 | Breillatt, Jr. |
| 4,310,509 | A | 1/1982 | Berglund |
| 4,323,557 | A | 4/1982 | Rosso |
| 4,595,001 | A | 6/1986 | Potter |
| 4,616,644 | A * | 10/1986 | Saferstein ........... A61F 13/0203 424/445 |
| 4,638,797 | A * | 1/1987 | Merrill ................ A61L 15/225 602/52 |
| 4,833,179 | A | 5/1989 | Young |
| 4,871,812 | A | 10/1989 | Lucast |
| 5,088,483 | A | 2/1992 | Heinecke |
| 5,120,781 | A | 6/1992 | Johnson, Jr. |
| 5,160,315 | A | 11/1992 | Heinecke |
| 5,209,971 | A | 5/1993 | Babu |
| 5,214,119 | A | 5/1993 | Leir |
| 5,531,855 | A | 7/1996 | Heinecke |
| 5,728,446 | A * | 3/1998 | Johnston ........... A61F 13/53704 428/167 |
| 5,834,008 | A | 11/1998 | Greenspan |
| 5,836,970 | A * | 11/1998 | Pandit ................ A61L 15/225 606/213 |
| 5,849,325 | A | 12/1998 | Heinecke |
| 5,908,693 | A | 7/1999 | Delgado |
| 5,965,154 | A * | 10/1999 | Haralambopoulos .. A61K 9/703 424/447 |
| 6,083,856 | A | 7/2000 | Joseph |
| 6,171,985 | B1 | 1/2001 | Joseph |
| 6,198,016 | B1 | 3/2001 | Lucast |
| 6,264,976 | B1 | 7/2001 | Heinecke |
| 6,441,082 | B1 | 8/2002 | Weitzel |
| 6,486,377 | B2 | 11/2002 | Rapp |
| 6,518,343 | B1 | 2/2003 | Lucast |
| 6,518,359 | B1 | 2/2003 | Clemens |
| 6,548,727 | B1 | 4/2003 | Swenson |
| 6,552,172 | B2 | 4/2003 | Marx |
| 6,607,799 | B1 | 8/2003 | Heinecke |
| 6,642,304 | B1 | 11/2003 | Hansen |
| 6,685,682 | B1 | 2/2004 | Heinecke |
| 7,008,647 | B2 * | 3/2006 | Burrell ................ A61K 9/0014 424/400 |
| 7,160,976 | B2 | 1/2007 | Luhmann |
| 7,226,657 | B1 | 6/2007 | Delmotte |
| 7,741,116 | B2 | 6/2010 | Boyce |
| 8,314,283 | B2 | 11/2012 | Kingsford |
| 2005/0186416 | A1 * | 8/2005 | Sebastian ................ C09J 11/06 428/343 |
| 2006/0159732 | A1 * | 7/2006 | Cullen .................... A61L 15/28 424/445 |
| 2007/0154509 | A1 | 7/2007 | Wilcher |
| 2008/0095830 | A1 | 4/2008 | Van Holten |
| 2010/0228174 | A1 * | 9/2010 | Huey ..................... A61L 15/44 602/44 |
| 2010/0247663 | A1 | 9/2010 | Day |
| 2010/0291219 | A1 * | 11/2010 | Karp ..................... A61K 35/32 424/489 |
| 2011/0112458 | A1 | 5/2011 | Holm |
| 2012/0070485 | A1 | 3/2012 | Soldani |
| 2012/0315303 | A1 | 12/2012 | Hezi-Yamit |
| 2012/0315305 | A1 | 12/2012 | Koopman |
| 2013/0123678 | A1 * | 5/2013 | Carty .................. A61F 13/0253 602/54 |

FOREIGN PATENT DOCUMENTS

| | | |
|---|---|---|
| WO | WO 1994-20133 | 9/1994 |
| WO | WO 1996-22115 | 7/1996 |
| WO | WO 1997-44015 | 11/1997 |
| WO | WO 1999-42146 | 8/1999 |
| WO | WO 2000-27327 | 5/2000 |
| WO | WO 2003-026544 | 4/2003 |
| WO | WO 2004-010913 | 2/2004 |
| WO | WO 2009-120432 | 10/2009 |
| WO | WO 2009-120433 | 10/2009 |
| WO | WO 2010-136588 | 12/2010 |

OTHER PUBLICATIONS

Boyce, "Design principles for composition and performance of cultured skin substitutes", Burns, 2001, vol. 27, pp. 523-533.

Geer, "Fibrin Promotes Migration in a Three-Dimensional in Vitro Model of Wound Regeneration" Tissue Engineering, 2002, vol. 8, No. 5, pp. 787-798.

Satas, "Handbook of Pressure Sensitive Adhesive Technology" 2nd Edition, 172 (1989).

Supp, "Engineered skin substitutes: practices and potentials", Clinics in Dermatology, 2005, vol. 23, pp. 403-412.

Zahedi, "A review on wound dressings with an emphasis on electrospun nanofibrous polymeric bandages", Polymer. Advanced Technologies, 2010, vol. 21, pp. 77-95.

International Search Report for PCT International Application No. PCT/US2014/042040, dated Sep. 11, 2014, 4pgs.

* cited by examiner

FIBRIN-COATED WOUND DRESSING

TECHNICAL FIELD

The present disclosure broadly relates to articles for treating wounds, and more specifically to wound dressing articles that include a fibrin powder layer on a suitable backing material.

BACKGROUND

Fibrinogen is cleaved and polymerized into fibrin using thrombin in a well-characterized process. Thrombin cleaves fibrinogen, forming fibrin monomers. Once fibrinogen is cleaved, fibrin monomers come together and form a covalently crosslinked fibrin network in the presence of factors, such as Factor XIII, normally present in blood. At a wound site, the fibrin network helps to close the wound and promote healing.

Various attempts have been made to provide fibrin in a form useful for treating wounds. Perhaps the most commonly known is the in situ generation of fibrin glue, typically performed by delivering separate solutions of fibrinogen and thrombin from a dual-barrel syringe.

International Patent Publication No. WO 97/44015 (Heath et al.) purportedly describes soluble microparticles including fibrinogen or thrombin, in free-flowing form. It is stated that these microparticles can be mixed to give a dry powder, to be used as a fibrin sealant that is activated only at a wound site.

Attempts have been made to provide a pre-formed fibrin material as a wound covering. For example, U.S. Pat. No. 6,486,377 B2 (Rapp et al.) purportedly describes a biodegradable, flexible wound covering based on fibrin and a process for its preparation, in which a fibrinogen solution is subjected to a single-stage or multi-stage dialysis, then a flexible fibrin web is formed by action of a thrombin solution on the fibrinogen solution and this is subsequently subjected to freeze-drying.

In another attempt, International Patent Publication No. WO 2009/120433 A2 (Delmotte et al.) purportedly describes making a fibrin wound dressing by mixing quantities of fibrinogen solution and thrombin solution with air. According to publication, the resulting foam is very light weight, and with the proper attention to the amount of thrombin, will rest on a vertical surface without dripping. The wound dressing may also be formulated for its ability to continue migration of healing substances, such as PDGF, from the dressing to the wound site. Thrombin substitutes, such as other clotting proteins, may be used instead of thrombin. The resulting foam can purportedly be lyophilized or ground and lyophilized for later reconstitution.

SUMMARY

There remains, however, a need for wound dressings and methods suitable for delivering fibrin to a wound bed, in order to accelerate re-epithelialization of the wound site. The present disclosure provides wound dressings that are convenient to use, do not require special low temperature storage conditions or two part delivery systems, and have advantages in the manufacture of terminally sterilized wound dressing articles.

In one aspect, the present disclosure includes a wound dressing article having a flexible film layer, a pressure-sensitive adhesive layer disposed on the flexible film layer, and a fibrin powder layer disposed on a surface of the pressure-sensitive adhesive layer opposite the flexible film layer.

In another aspect, the present disclosure includes a method of making a wound dressing article, the method comprising providing a flexible film layer, disposing a pressure-sensitive adhesive layer on the flexible film layer, and forming a fibrin powder layer on a surface of the pressure-sensitive adhesive layer opposite the flexible film layer to prepare the wound dressing article.

In another aspect, the present disclosure includes a method of treating a wound, the method including applying a wound dressing article of the present disclosure to an external wound on a mammal. In some embodiments, the mammal is a human.

In an aspect of the present disclosure, the wound dressing is adapted to form a covering or bandage for minor abrasions, cuts, scrapes, scratches, burns, sunburns, ulcers and other skin injuries and irritations.

The above summary of the present disclosure is not intended to describe each embodiment of the present invention. The details of one or more embodiments of the invention are also set forth in the description below. Other features, objects, and advantages of the invention will be apparent from the description and from the claims.

Figure 1:
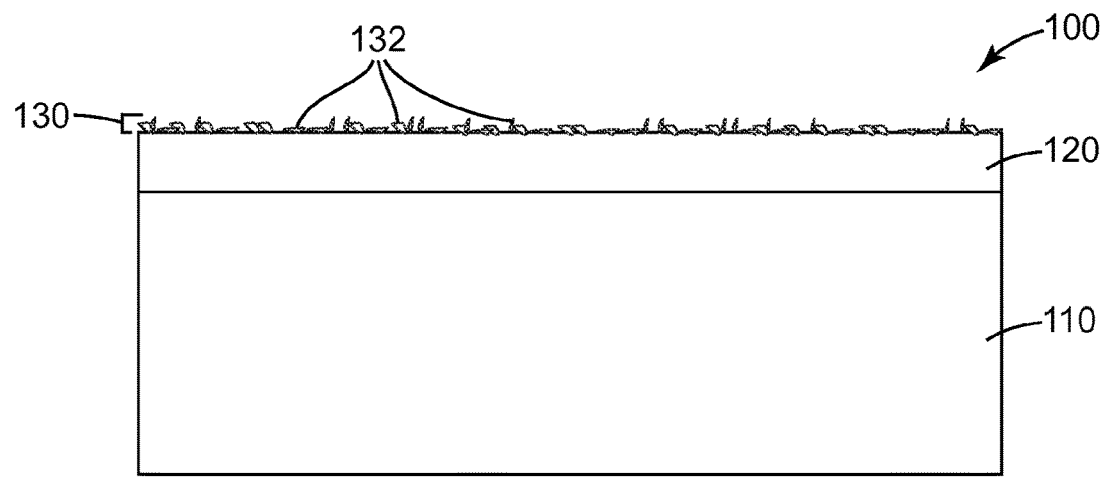
FIG. 1 is a schematic cross-section of an exemplary embodiment of a wound dressing article according to the present disclosure.

It should be understood that numerous other modifications and embodiments can be devised by those skilled in the art, which fall within the scope and spirit of the principles of the disclosure. The figures may not be drawn to scale.

DETAILED DESCRIPTION

Unless otherwise noted, all parts, percentages, ratios, etc. in the Examples and the rest of the specification are by weight.

As used herein, forms of the words "comprise", "have", and "include" are legally equivalent and open-ended. Therefore, additional non-recited elements, functions, steps or limitations may be present in addition to the recited elements, functions, steps, or limitations.

In the art, the term "fibrin" has unfortunately been used to refer to fibrin itself as well as fibrin precursors. Fibrin precursors can include, for example, "fibrinogen". It is generally understood by those skilled in the art that the terms "fibrin" and "fibrinogen" do not literally refer to a single species. The terms "fibrin" and "fibrinogen" instead refer to product and precursor protein species, respectively. More specifically, fibrinogen is a precursor to fibrin. In some instances, the term "fibrin(ogen)" has been used when the intent is to refer to fibrin and/or fibrinogen. Thus, it is evident that care needs to be taken in understanding what is meant by the term "fibrin".

Further confusion of terminology can arise, due to use of the terms "fibrin sealant" or "fibrin glue" in reference to an in situ combination of fibrinogen and thrombin to form a sealant or glue. The combination of fibrinogen and thrombin is well known to produce fibrin under suitable conditions (e.g., moisture and certain salts), and such a combination is typically used for in situ generation of a "fibrin sealant" or "fibrin glue", useful for example as a wound sealant or a hemostatic agent. The in situ generation of fibrin glue typically involves delivery of separate aqueous solutions of fibrinogen or thrombin from separate barrels of a double-barrel syringe (analogous to the use of double-barrel syringe devices in the delivery of the separate components of a two-part epoxy adhesive). Those having skill in the art will recognize that such in situ generation of a hydrated fibrin glue or sealant is quite different from providing an article that includes a layer of dry fibrin powder disposed on a layer of pressure-sensitive adhesive, which is in turn disposed on a flexible film layer.

The term "dry powder fibrin sealant" has sometimes been used by others for describing a mixture of fibrinogen particles (or microparticles) and thrombin particles (or microparticles). As already mentioned, fibrinogen is well known as a precursor to fibrin, and thrombin is well known to act on fibrinogen to convert fibrinogen to fibrin, under suitable conditions. Since the reaction of fibrinogen and thrombin to produce fibrin typically requires moisture and various salts, it is conceivable to formulate a dry powder having particles of fibrinogen and thrombin mixed together as a stable formulation of fibrin precursors, as is purportedly described for the preparation of a "dry powder fibrin sealant" (see, for example, U.S. Published Patent Application No. 2012/0315303). However, the term "fibrin powder", as used in the present disclosure, refers to a powder having particles that contain fibrin. Thus, the term "fibrin powder" as used herein is distinguishable from reference to a dry powder fibrin sealant composition having fibrinogen particles mixed with thrombin particles.

FIG. 1 illustrates an exemplary embodiment of a wound dressing article 100 of the present disclosure. Wound dressing article 100 includes a flexible film layer 110, a pressure-sensitive adhesive ("PSA") layer 120 disposed on flexible film layer 110, and a fibrin powder layer 130 disposed on a surface of pressure-sensitive adhesive layer 120 opposite flexible film layer 110. Fibrin powder layer 130 includes fibrin powder particles 132. It will be understood that the wound dressing article can have additional, intervening layers (for example, an absorbent foam layer) disposed between flexible film layer 110 and PSA layer 120. Wound dressing articles of the present disclosure are useful, for example, for accelerating wound healing. The delivery of a fibrin layer to a wound site can be particularly useful for promoting re-epithelialization of wounds that otherwise lack a fibrin layer at some portion of the wound site.

The fibrin powder particles are adhered to the wound dressing article. By adhering the fibrin powder to a PSA layer on the wound dressing, it is possible to remove wound exudates from the wound (e.g., by aspiration) during early stages of healing without also removing the fibrin powder. In this way, the fibrin powder can be kept in place at the wound site in order to promote re-epithelialization of the wound.

In some embodiments, the fibrin powder layer comprises fibrin powder particles disposed primarily on the wound-facing surface of the pressure-sensitive adhesive layer. In some other embodiments, some of the fibrin powder particles can also be included within the layer of pressure-sensitive adhesive, although this is not a requirement.

The fibrin powder particles can have a variety of morphologies. The fibrin powder particles can be, for example, microspheres, amorphous particles, or any mixture thereof. The size of the fibrin powder particles is not required to be particularly limited. In some embodiments, the fibrin powder layer includes fibrin powder particles having an average particle size in largest dimension in a range of 0.1 micrometer up to 100 micrometers. The fibrin powder particles can have an average particle size, of at least 0.1 micrometer, at least 1 micrometer, at least 2 micrometers, at least 5 micrometers, or even at least 10 micrometers. The average particle size can be bounded by an upper limit of, for example, up to 1000 micrometers, up to 500 micrometers, up to 200 micrometers or even up to 100 micrometers.

The fibrin powder layer can have any coating weight that is sufficient to be effective in promoting wound re-epithelialization. In some embodiments, the coating weight of the fibrin powder layer is in a range from 0.2 to 20 milligrams per $cm^2$, from 0.5 to 10 milligrams per $cm^2$, or even from about 1 to 5 milligrams per $cm^2$. In some embodiments, the coating weight of the fibrin powder layer is about 2 milligrams per $cm^2$.

A fibrin powder layer of the present disclosure may include an amount of fibrin in a range from 1 weight percent to 99 weight percent relative to a total weight of the fibrin powder layer, or any amount within that range. More preferably, the fibrin powder layer includes fibrin in a range from 2 weight percent to 20 weight percent, or even more preferably in a range from 4 weight percent to 8 weight percent, relative to a total weight of the fibrin powder layer.

A fibrin powder suitable for the fibrin powder layer 130 can be prepared by combining aqueous solutions of fibrinogen and thrombin, including NaCl and $CaCl_2$ salts, to obtain a fibrin gel. The fibrin gel so obtained can be dried (e.g., by lyophilization) and then milled or otherwise processed to obtain a powder of fibrin particles.

Other suitable fibrin powder particles and methods of making such particles can include, for example, fibrin nanoparticles and fibrin microbeads and methods of making these (e.g., see U.S. Pat. No. 6,552,172 (Marx et al.)), and fibrin-based microcarriers and methods of making these (see, e.g., U.S. Published Patent Application No. 2010/0291219 (Karp et al.)).

In some embodiments, methods used for making fibrin powder particles are not dependent on oil-in-water emulsions and thus do not require additional steps of oil removal which often times requires the use of organic solvents. A fibrin powder that is produced free of organic solvents and/or oil and would typically be considered more compatible and suitable for human use.

Thus, the invention provides a method for making a fibrin powder composition by combining (or mixing or physically contacting) fibrinogen and thrombin to form fibrin, as a first step. Any suitable sources of fibrinogen and thrombin can be used in the preparation of the fibrin powder. For example, the species from which the fibrinogen is obtained could be human, bovine, porcine, or other animal sources. Similarly, thrombin can also be obtained from human, bovine, porcine, or other animal sources. Fibrinogen and thrombin can be obtained commercially as aqueous solutions, and the concentrations of these solutions may vary. Alternatively, fibrinogen and thrombin can be provided in lyophilized form and stored at very low temperatures. Lyophilized fibrinogen is typically reconstituted with sterile water before use. Thrombin is also reconstituted with sterile calcium chloride and water before use. Saline, phosphate buffered solution, or other reconstituting liquid can also be used. In preparing fibrin, the reconstituted fibrinogen and thrombin are then combined to form fibrin. The Examples section of the present disclosure describes a combination of fibrinogen solution and thrombin solution to give a final concentration of 5.3 weight percent of fibrinogen and 0.281 IU of thrombin. Other suitable final concentrations are also contemplated ranging from 0.1-40 mg/mL fibrinogen. Fibrinogen and thrombin may be purchased commercially from suppliers such as Sigma-Aldrich (Milwaukee, Wis.).

Fibrinogen and thrombin solutions are generally aqueous in nature, giving rise to a resultant fibrin hydrogel when combined. This fibrin hydrogel is then dehydrated using any number of methods. This step may be referred to as dehydrating, drying or desiccating the hydrogel, all of which refer herein to the process of removing as much of the water content from the hydrogel as possible. Dehydration can therefore be accomplished using heat, vacuum, lyophilization, desiccation, and the like. In some embodiments, lyophilization may be preferred since the resulting fibrin material is less likely to swell once in contact with an aqueous solution. The dehydration step may occur over a range of time, depending on the particular method used and the volume of the hydrogel. For example, the step may last for a few minutes, a few hours, or a few days. The present disclosure is not intended to be limited in this regard.

Once the hydrogel is dehydrated, it can be processed to form fibrin powder particles. The dehydrated hydrogel may be ground, pulverized, milled, crushed, granulated, pounded, and the like, provided the effect is to produce fibrin powder.

In some embodiments, the method of preparing the fibrin powder particles does not require emulsions and thus does not involve removal of oils with, for example, organic solvents. Such a method may be referred to as a "non-emulsion" method. The fibrin powder particles so produced are therefore free of oil and also free of organic solvents. The presence of oil and/or organic solvents may be determined through a chemical analysis of the fibrin powder. As an example, the fibrin powder may be placed in an aqueous or organic solution, thereby allowing constituents to leach out and into the solution. The solution can then be tested for the presence of oil and/or organic solvents using, for example, mass spectrometry, HPLC, or any other suitable chemical analysis method, as will be known to those of ordinary skill in the art.

The method may further involve size separating the fibrin powder particles. This may be accomplished most easily by sieving the particle composition through one or more appropriate sieves or filters having desired pore sizes. In some embodiments the powder particles can be sieved to arrive at populations having average diameters in the range of about 85-180, 90-170, 100-160, 100-150, 110-150, 120-140, or about 130 micrometers in average diameter. The powder particles may be equal to or less than 80, 90, 100, 110, 120, 130, 140, 150, 160, 170, or 180 micrometers, provided they have a minimum average diameter of at least 10, 20, 30, 40 or 50 micrometers. It is to be understood that these average diameters refer to the diameter of the dehydrated particles rather than their rehydrated diameters. The particle volume may increase 10-250% of the initial volume after rehydration.

In some embodiments, fibrin powder particles can be size restricted. In some aspects, the composition comprises a plurality of fibrin powder particles, wherein at least 50% of which have an average diameter of 85-180 micrometers prior to hydration. In some embodiments, at least 55%, at least 60%, at least 65%, at least 70%, at least 75%, at least 80%, at least 85%, at least 90%, at least 95%, or more of the fibrin powder particles have an average diameter of 85-180 micrometers.

The fibrin powder particles produced by this method are typically of irregular shape and size. That is, for the most part these particles are not spherical. As a result, the diameter of each particle can be determined by summing its longest and its shortest dimension and dividing that sum by two. This is referred to as the average diameter of a single particle. Average diameter of a population of particles may be deduced based on a sieving analysis (i.e., the sieving analysis would provide a range of average diameters based on retention and/or flow through of particles). It will be understood that the term "average diameter" of a population of particles, defined as "summing its longest and its shortest dimension and dividing that sum by two", is conceptually similar to the term "average particle size", which refers to the "largest dimension" of the particles in a population of the particles.

In some embodiments, fibrin powder particles are provided that are defined by their surface topology, topography, or roughness. This surface topology or roughness may be expressed in terms of the number and/or size of features (or protrusions) on the surface of the particles. Roughness can be observed using techniques commonly used in the art including optical profilometry and atomic force microscopy. The number of features on these particles may range from 2-100 typically. The size of these features (or protrusions) may be expressed in terms of absolute length or in terms of the ratio of the size of the feature (or protrusion) and the average diameter of the particles. In some embodiments, the size of the feature is about 1 micrometer, about 2 micrometers, about 3 micrometers, about 4 micrometers, about 5 micrometers, about 6 micrometers, about 7 micrometers, about 8 micrometers, about 9 micrometers, about 10 micrometers, or more. In other embodiments, the size of the feature is more than 10 micrometers, more than 15 micrometers, more than 20 micrometers, more than 25 micrometers, more than 30 micrometers, more than 35 micrometers, more than 40 micrometers, more than 45 micrometers, more than 50 micrometers, or more. In still other embodiments, the size is 10-100 micrometers. In other embodiments, the size is 1-10 micrometers. The ratio of feature size and particle average diameter may be about 5%, 10%, 15%, 20%, 25%, 30%, 35%, 40%, 45%, or 50%, or more. This surface roughness is important since it has been found that cells such as connective tissue progenitor cells are better able to bind to particles having a greater degree of surface roughness.

The fibrin powder layer can include additives. Examples of additives can include any of antimicrobial agents, anti-inflammatory agents, topical anesthetics (e.g., lidocaine), other drugs, growth factors, polysaccharides, glycosaminoglycans. If an additive is included, it should be included at a level that does not interfere with the activity of the fibrin powder layer with respect to promoting healing of the wound.

Antimicrobial agents are agents that inhibit the growth of or kill microbes such as bacteria, mycobacteria, viruses, fungi, and parasites. Anti-microbial agents therefore include anti-bacterial agents, anti-mycobacterial agents, anti-viral agents, anti-fungal agents, and anti-parasite agents. Fibin powder layers so loaded can be used to prevent or control infection.

Anti-inflammatory agents are agents that reduce or eliminate inflammation. Examples include alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, and zomepirac sodium.

Various PSAs can be used to form pressure-sensitive adhesive layer 120 on the flexible film layer 110 to make it adhesive. For example, PSAs may be formulated to offer good skin adhesion characteristics, offer excellent conformability, and provide a gentle release from the skin and wound site. The PSA layer can be continuous, discontinuous, pattern coated, or melt-blown, for example.

One well known means of identifying PSAs is the Dahlquist criterion. This criterion defines a PSA as an adhesive having a 1 second creep compliance of greater than $1 \times 10^{-6}$ cm$^2$/dyne, as described in Handbook of PSA Technology, Donatas Satas (Ed.), 2nd Edition, p. 172, Van Nostrand Reinhold, New York, N.Y., 1989. Alternatively, since modulus is, to a first approximation, the inverse of creep compliance, PSAs may be defined as adhesives having a Young's modulus of less than $1 \times 10^6$ dynes/cm$^2$. Another well known means of identifying a PSA is that it is aggressively and permanently tacky at room temperature and firmly adheres to a variety of dissimilar surfaces upon mere contact without the need of more than finger or hand pressure, and which may be removed from smooth surfaces without leaving a residue as described in Glossary of Terms Used in the Pressure Sensitive Tape Industry provided by the Pressure Sensitive Tape Council, 1996. Another suitable definition of a suitable PSA is that it preferably has a room temperature storage modulus within the area defined by the following points as plotted on a graph of modulus versus frequency at 25° C.: a range of moduli from approximately $2 \times 10^5$ to $4 \times 10^5$ dynes/cm$^2$ at a frequency of approximately 0.1 radian/sec (0.017 Hz), and a range of moduli from approximately $2 \times 10^6$ to $8 \times 10^6$ dynes/cm$^2$ at a frequency of approximately 100 radians/sec (17 Hz) (for example see FIG. 8-16 on p. 173 of Handbook of PSA Technology (Donatas Satas, Ed.), 2nd Edition, Van Nostrand Rheinhold, New York, 1989). Any of these methods of identifying a PSA may be used to identify suitable PSAs for use in the methods of the present invention.

Examples of PSAs useful in the present invention include rubber based adhesives (e.g., tackified natural rubbers, synthetic rubbers, and styrene block copolymers), (meth)acrylics (e.g., (meth)acrylates), poly(alpha-olefins), polyurethanes, and silicones Amine containing polymers can also be used which have amine groups in the backbone, pendant thereof, or combinations thereof. A suitable example includes a poly(ethyleneimine).

Some polymers may be chemically modified to include the desired amount of acid or base functionality. Alternatively, the polymers can be made with acid or base-functional monomers. Alternatively or additionally, the PSAs can include acid- or base-functional additives, such as tackifiers, plasticizers, or other additives.

Useful natural rubber PSAs generally contain masticated natural rubber, from 25 parts to 300 parts of one or more tackifying resins to 100 parts of natural rubber, and typically from 0.5 part to 2.0 parts of one or more antioxidants. Natural rubber may range in grade from a light pale crepe grade to a darker ribbed smoked sheet and includes such examples as CV-60, a controlled viscosity rubber grade and SMR-5, a ribbed smoked sheet rubber grade. Tackifying resins used with natural rubbers generally include but are not limited to wood rosin and its hydrogenated derivatives; terpene resins of various softening points, and petroleum-based resins. Other materials can be added to natural rubber adhesives for special purposes, wherein the additions can include plasticizers, pigments, and curing agents to partially vulcanize the PSA. Examples of acid-modified tackifiers include acid-modified polyhydric alcohol resin ester tackifiers as described in U.S. Pat. No. 5,120,781 (Johnson).

Another useful class of PSAs is those that include synthetic rubber. Such adhesives are generally rubbery elastomers, which are either self-tacky or non-tacky that require tackifiers. Examples of acid-modified tackifiers include acid-modified polyhydric alcohol rosin ester tackifiers as described in U.S. Pat. No. 5,120,781 (Johnson). Self-tacky synthetic rubber PSAs can include, for example, butyl rubber, a copolymer of isobutylene with less than 3 percent isoprene, polyisobutylene, a homopolymer of isoprene, polybutadiene, or styrene/butadiene rubber.

Synthetic rubber PSAs, that generally require tackifiers, are also usually easier to melt process. They include polybutadiene or styrene/butadiene rubber, from 10 parts to 200 parts of a tackifier, and generally from 0.5 parts to 2.0 parts per 100 parts rubber of an antioxidant. An example of a synthetic rubber is that available from BF Goodrich under the trade name AMERIPOL 101 IA, a styrene/butadiene rubber. Tackifiers that are useful include derivatives of rosins, polyterpenes, C5 aliphatic olefin-derived resins, and C9 aromatic/aliphatic olefin-derived resins.

Styrene block copolymer PSAs generally include elastomers of the A-B or A-B-A type, where A represents a thermoplastic polystyrene block and B represents a rubbery block of polyisoprene, polybutadiene, or poly(ethylene/butylene), and resins. Examples of the various block copolymers useful in block copolymer PSAs include linear, radial, star and tapered styrene-isoprene block copolymers such as those available under the trade names KRATON D 1107P, KRATON G1657, KRATON G 1750X, and KRATON D 1118X from Shell Chemical Co., Deer Park, Tex. The polystyrene blocks tend to form domains in the shape of spheroids, cylinders, or plates that causes the block copolymer PSAs to have two phase structures. Resins that associate with the rubber phase generally develop tack in the PSA. Examples of rubber phase associating resins include aliphatic olefin-derived resins, such as those available under the trade names ESCOREZ 1300 and WINGTACK from Goodyear, Akron, Ohio; rosin esters, such as those available under the trade names FORAL and STAYBELITE Ester 10 from Hercules, Inc., Wilmington, Del.; hydrogenated hydrocarbons, such as those available under the trade name ESCOREZ 5000 from Exxon, Irving, Tex.; polyterpenes, such as those available under the trade name PICCOLYTE A; and terpene phenolic resins derived from petroleum or turpentine sources, such as those available under the trade name PICCOFYN A100 from Hercules, Inc. rosins that associate with the thermoplastic phase tend to stiffen the PSA.

In preferred PSAs of the present invention, acrylate and methacrylate monomers and polymers can be used and are referred to collectively herein as "(meth)acrylate" or "(meth)acrylic" monomers and polymers. (Meth)acrylate polymers may be copolymers, optionally in combination with other, non-(meth)acrylate, e.g., vinyl-unsaturated, monomers. Such polymers and their monomers are well-known in the polymer and adhesive arts, as are methods of preparing the monomers and polymers. One of skill will understand and recognize that such polymers can be useful to impart adhesive properties, and will understand their use in providing an adhesive as described herein.

(Meth)acrylic PSAs generally have a glass transition temperature of about −20° C. or less and may include from 100 to 60 weight percent of a C4-C12 alkyl ester component such as, for example, isooctyl acrylate, 2-ethyl-hexyl acrylate and n-butyl acrylate and from 0 to 40 weight percent of a polar component such as, for example, acrylic acid, methacrylic acid, ethylene, vinyl acetate, N-vinyl pyrrolidone and styrene macromer.

Suitable acidic monomers for preparing (meth)acrylic PSAs include those containing carboxylic acid functionality such as acrylic acid, methacrylic acid, itaconic acid, and the like; those containing sulfonic acid functionality such as 2-sulfoethyl methacrylate; and those containing phosphonic acid functionality. Preferred acidic monomers include acrylic acid and methacrylic acid.

Additional useful acidic monomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, B-carboxyethyl acrylate, 2-sulfoethyl methacrylate, styrene sulfonic acid, 2-acrylamido-2-methylpropane sulfonic acid, vinyl phosphonic acid, and the like, and mixtures thereof.

Due to their availability, acidic monomers of the present invention are typically the ethylenically unsaturated carboxylic acids. When even stronger acids are desired, acidic monomers include the ethylenically unsaturated sulfonic acids and ethylenically unsaturated phosphonic acids. Sulfonic and phosphonic acids generally provide a stronger interaction with a basic polymer. This stronger interaction can lead to greater improvements in cohesive strength, as well as higher temperature resistance and solvent resistance of the adhesive.

Suitable basic monomers for preparing (meth)acrylic PSAs include those containing amine functionality such as vinyl pyridine, N,N-diethylaminoethyl methacrylate, N,N-dimethylamino-ethyl methacrylate, N,N-diethylaminoethyl acrylate, N,N-dimethylaminoethyl acrylate, and N-t-butylaminoethyl methacrylate. Preferred basic monomers include N,N-dimethylaminoethyl methacrylate, and N,N-dimethylaminoethyl acrylate.

The (meth)acrylic PSAs may be self-tacky or tackified. Useful tackifiers for (meth)acrylics are rosin esters such as that available under the trade name FORAL 85 from Hercules, Inc., aromatic resins such as that available under the trade name PICCOTEX LC-55WK from Hercules, Inc., aliphatic resins such as that available under the trade name PICCOTAC 95 from Hercules, Inc., and terpene resins such as that available under the trade names PICCOLYTE A-115 and ZONAREZ B-100 from Arizona Chemical Co. Other materials can be added for special purposes, including hydrogenated butyl rubber, pigments, and curing agents to vulcanize the adhesive partially. Examples of acid-modified tackifiers include acid-modified polyhydric alcohol rosin ester tackifiers as described in U.S. Pat. No. 5,120,781 (Johnson).

Poly(alpha-olefin) PSAs, also called a poly(l-alkene) PSAs, generally include either a substantially uncrosslinked polymer or a uncrosslinked polymer that may have radiation activatable functional groups grafted thereon as described in U.S. Pat. No. 5,209,971 (Babu et al.). The poly(alpha-olefin) polymer may include one or more tackifying materials, not only to improve adhesive properties but also provide the necessary acidic or basic functional groups needed for this application. Tackifying materials are typically resins that are miscible in the poly(alpha-olefin) polymer. The total amount of tackifying resin in the poly(alpha-olefin) polymer ranges from 0 to 150 parts by weight per 100 parts of the poly (alpha-olefin) polymer depending on the specific application. Useful tackifying resins include resins derived by polymerization of C5 to C9 unsaturated hydrocarbon monomers, polyterpenes, synthetic polyterpenes and the like. Examples of such commercially available resins based on a C5 olefin fraction of this type include those available under the trade name WINGTACK from Goodyear Tire and Rubber Co. Other materials can be added for special purposes, including antioxidants, fillers, pigments, and radiation activated crosslinking agents.

Another useful class of PSAs can include polyurethanes. Polyurethanes may be produced by reacting a polyisocyanate with a polyalcohol (polyol). As described herein, a polyisocyanate is a molecule with two or more isocyanate functional groups and a polyalcohol is a molecule with two or more hydroxyl functional groups. The reaction product is a polymer containing urethane linkages. The functional groups can be alkanes, esters, ethers, and other components.

Isocyanates can be classed as aromatic, such as diphenylmethane diisocyanate (MDI) or toluene diisocyanate (TDI); or aliphatic, such as hexamethylene diisocyanate (HDI) or isophorone diisocyanate (IPDI). An example of a polymeric isocyanate is polymeric diphenylmethane diisocyanate, which is a blend of molecules with two-, three-, and four- or more isocyanate groups, with an average functionality of 2.7. Isocyanates can be further modified by partially reacting them with a polyol to form a prepolymer. A quasi-prepolymer is formed when the stoichiometric ratio of isocyanate to hydroxyl groups is greater than 2:1. A true prepolymer is formed when the stoichiometric ratio is equal to 2:1. Important characteristics of isocyanates include the molecular backbone, % NCO content, functionality, and viscosity.

Polyols are distinguished from short chain or low-molecular weight glycol chain extenders and cross linkers such as ethylene glycol (EG), 1,4-butanediol (BDO), diethylene glycol (DEG), glycerine, and trimethylol propane (TMP). Polyols are formed by base-catalyzed addition of propylene oxide (PO), ethylene oxide (EO) onto a hydroxyl or amine containing initiator, or by polyesterification of a di-acid, such as adipic acid, with glycols, such as ethylene glycol or dipropylene glycol (DPG). The choice of initiator, extender, and molecular weight of the polyol greatly affect its physical state, and the physical properties of the polyurethane polymer. Important characteristics of polyols include the molecular backbone, initiator, molecular weight, % primary hydroxyl groups, functionality, and viscosity. Examples of suitable polyurethanes adhesives include those in U.S. Pat. No. 7,160,976 (Luhmann et al.), U.S. Pat. No. 6,642,304 (Hansen et. al), and U.S. Pat. No. 6,518,359 (Clemens et al.).

Silicone PSAs include two major components, a polymer or gum, and a tackifying resin. The polymer is typically a high molecular weight polydimethylsiloxane or polydimethyldiphenylsiloxane, that contains residual silanol functionality (SiOH) on the ends of the polymer chain, or a block copolymer including polydiorganosiloxane soft segments and urea terminated hard segments. The tackifying resin is generally a three-dimensional silicate structure that is end-capped with trimethylsiloxy groups (OSiMe$_3$) and also contains some residual silanol functionality. Examples of tackifying resins include SR 545, from General Electric Co., Silicone Resins Division, Waterford, N.Y., and MQD-32-2 from Shin-Etsu Silicones of America, Inc., Torrance, Calif. Manufacture of typical silicone PSAs is described in U.S. Pat. No. 2,736,721 (Dexter). Manufacture of silicone urea block copolymer PSA is described in U.S. Pat. No. 5,214,119 (Leir et al.).

In some embodiments, the adhesive contains greater than 0.42 mmol of acidic- or basic-functional groups per gram of PSA that can be neutralized by addition of a MVTR-modifying material (e.g., see U.S. Published Patent Application No. 2011/0112458). More preferably, the adhesive contains at least 0.69 mmol of these functional groups per gram of PSA. Even more preferably, the adhesive contains 0.84 mmol of these functional groups. Even more preferably, the adhesive contains at least 1.3 mmoles of these functional groups. Even more preferably, the adhesive contains at least 1.80 mmol of these functional groups. Even more preferably, the adhesive contains at least 2.08 mmoles of these functional groups. In most embodiments, the adhesive contains between 1.3 mmol and 2.5 mmoles of these functional groups.

Preferably, the adhesive should contain no greater than 5.6 mmoles of these functional groups per gram of PSA. More preferably, the adhesive contains no greater than 4.2 mmoles of these functional groups per gram of PSA, and even more preferably no greater than 2.8 mmoles of these functional groups per gram of PSA.

In some embodiments wherein the PSA contains a polymer formed from acidic monomers, the corresponding weight percents may be considered. Preferably, the PSA contains greater than 3 weight percent of a monomer unit in the adhesive polymer that contains acid/base functional groups that can be neutralized by a MVTR-modifying material. More preferably, the PSA contains at least 6 weight percent of these functionalized monomer units. Even more preferably, the PSA contains at least 9 weight percent of these functionalized monomer units. Even more preferably, the PSA contains at least 10 weight percent of these functionalized monomer units. Even more preferably, the PSA contains at least 12 weight percent of these functionalized monomer units. Preferably, the PSA should contain no greater than 40 weight percent of the functionalized monomer units. More preferably the PSA contains no greater than 30 weight percent, even more preferably no greater than 25 weight percent of the functionalized monomer units, and most preferably no greater than 20 based on the total weight of the monomers used in the polymer used to make the PSA. Preferably, such values apply to (meth)acrylate polymers.

In certain embodiments, the PSA may include additional hydrophilic polymer components. These hydrophilic polymer components of the PSA are distinct from plasticizers or other additives that may be used in the adhesive to tackify or otherwise affect properties of the adhesive. The hydrophilic polymer component may be reactive or nonreactive with the adhesive monomers in the PSA. If the hydrophilic polymer is nonreactive (i.e., not incorporated into the polymer chain) the molecular weight of the hydrophilic polymer component is greater than 1000. More preferably, the molecular weight is greater than 2000.

When present in the adhesive, the hydrophilic polymer components are generally present in amounts no greater than 30 weight percent, based on the total weight of the PSA. In those adhesives that include a hydrophilic polymer component, lower concentrations of acid- or basic-functional groups in the PSA may be needed to impact a significant increase in MVTR when a MVTR-modifying material is incorporated into a medical article including the PSA, in comparison to a PSA of the same mass concentration of acid- or basic-functional groups that does not include the hydrophilic polymer components. For example, a PSA with 10 weight percent acid functional groups and 10 weight percent of additional hydrophilic component(s) may show a greater increase in MVTR when exposed to an appropriate MVTR-modifying material by comparison to a PSA with only 10 weight percent acid functional groups and no additional hydrophilic components. The combined weight percent of reactive groups (e.g., acid) and hydrophilic polymer components in the PSA is preferably at least 15%, more preferably at least 20%, and most preferably at least 24% by weight of the PSA. For example, if the adhesive contains 6% acid groups, then the hydrophilic component should be at least 9% by weight, more preferably at least 14% by weight, and most preferably at least 18% by weight. If the adhesive group contains 12 weight % acrylic acid, the hydrophilic component should be at least 3% by weight, more preferably at least 8% by weight, and most preferably at least 12% by weight of the PSA.

In certain embodiments, the ratio of the hydrophobic polymer component(s) in the PSA to the hydrophilic polymer component(s) in the PSA is preferably at least 1.5:1. More preferably at least 1.9:1, even more preferably 2.3:1. In most embodiments, less than 6:1.

In certain embodiments, an exemplary nonreactive hydrophilic polymer component includes one or more poly(alkylene oxide) copolymers. The poly(alkylene oxide) copolymers can be combined with the PSA monomers (e.g., (meth)acrylate monomers or other acidic monomers) or with the copolymer formed from the PSA monomers. The poly (alkylene oxide) copolymers generally do not migrate to the extent of phase separation between the copolymerized acrylate monomers and the poly(alkylene oxide) copolymer. By "phase separation" or "phase separate," it is meant that visible crystallization or liquid regions do not appear in the adhesive solution or bulk adhesive.

In preferred embodiments, the poly(alkylene oxide) copolymers include at least two copolymerized alkylene oxide monomers, at least one of which is hydrophilic and at least one of which is hydrophobic. A preferred copolymer is formed from ethylene oxide and propylene oxide. They can be random, alternating, or block. Preferably, they are block copolymers that include hydrophobic and hydrophilic segments. Particularly useful poly(alkylene oxide) copolymers have a weight average molecular weight of about 1000 to about 15,000, preferably of about 3000 to about 12,000.

Preferred poly(alkylene oxide) copolymers have appreciable water solubility, preferably, at least about 10 parts per 100 parts of water, exhibit surfactant characteristics preferably having an HLB (hydrophilic lipophilic balance) value of about 3 to about 15, and more preferably, about 5 to about 12. Useful poly(alkylene oxide) copolymers have ratios of hydrophilic monomers (e.g., ethylene oxide) to hydrophobic monomers (e.g., propylene oxide) of from about 90:10 to about 10:90, more preferably, from about 80:20 to about 30:70.

Monomers that may be used to make poly(alkylene oxide) copolymers include ethylene oxide and related glycols as a hydrophilic component and propylene oxide, butylene oxide, trimethylene oxide, tetramethylene oxide and the like and related glycols as a hydrophobic component. The poly(alkylene oxide) copolymers may be terminated with lower alkyl groups, amino groups, hydroxyl groups, carboxylic acid groups, aromatic groups, or other nonreactive groups.

Examples of useful poly(alkylene oxide) copolymers include, but are not limited to, those poly(alkylene oxide) copolymers available under the trade designations TETRONIC (tetrafunctional block copolymers derived from sequential addition of propylene oxide and ethylene oxide to ethylene diamine with hydrophilic endblocks) and TETRONIC R (tetrafunctional block copolymers derived from sequential addition of propylene oxide and ethylene oxide to ethylene diamine with hydrophobic endblocks) copolymers available from BASF, Mt. Olive, N.J.; PLURONIC (triblock copolymers with poly(ethylene oxide) end blocks and poly(propylene oxide) midblock) and PLURONIC R (triblock copolymers with poly(propylene oxide) endblocks and poly(ethylene oxide) midblock) copolymers available from BASF; UCON Fluids (random copolymers of ethylene oxide and propylene oxide) available from Union Carbide, Danbury, Conn. Various combinations of poly(alkylene oxide) copolymers can also be used. Preferred nonreactive hydrophilic polymer components are block copolymers of polyethylene glycol and propylene glycol available from BASF, Germany under the trade name PLURONIC.

Preferably, the poly(alkylene oxide) copolymer can be used in an amount of at least about 5 weight percent (wt. %), based on the total weight of the adhesive composition (e.g., the copolymerized (meth)acrylate/hydrophilic acidic comonomers and poly(alkylene oxide) copolymer). More preferably, the poly(alkylene oxide) copolymer is used in an amount of at least about 10 wt. %, and most preferably, at least about 15 wt. %. Preferably, the poly(alkylene oxide) copolymer can be used in an amount of no greater than about 30 wt. %. The amount of poly(alkylene oxide) copolymer required depends upon the type and ratios of the (meth) acrylate and hydrophilic acidic comonomers employed in the polymerizable mixture and the type and molecular weight of the poly(alkylene oxide) copolymer used in the adhesive composition.

In other embodiments, an exemplary reactive hydrophilic polymer component includes a hydrophilic macromolecular monomer which has a vinyl group copolymerizable with the PSA monomers. The hydrophilic macromolecular monomer contains a plurality of hydrophilic sites which impart the required hydrophilicity to the monomer. The hydrophilic macromolecular monomer may be represented by the general Formula (I):

X—Y—Z  (I)

wherein X is a vinyl group copolymerizable with the PSA monomers, Y is a divalent linking group, and Z is a monovalent polymeric moiety, i.e., containing two or more monomer units, comprising a polyether essentially unreactive under the free radical initiated, copolymerizing conditions employed to form the pressure-sensitive adhesive terpolymer.

The preferred X group is of the general Formula (II):

wherein $R^a$ is a hydrogen atom or a methyl group.
The preferred Y group is a

group (i.e., a divalent carbonyl group).
The preferred Z moiety is a monovalent polyether of the general formula (III):

—W—OR$^b$  (III)

wherein $R^b$ is hydrogen, lower alkyl, phenyl, or substituted phenyl; and W is a divalent poly(lower alkylene oxide) group containing 2 to about 250 repeating alkoxy units and selected from the group consisting of a poly(ethylene oxide) radical, a poly(propylene oxide) radical, a radical of a copolymer of ethylene oxide and propylene oxide, and a poly(tetramethylene oxide) radical. In a preferred hydrophilic macromonomer, a monovalent polyether of Formula (III) is bonded covalently to the carbonyl group (i.e., where Y is divalent carbonyl) through a terminal oxygen atom contained in the W moiety.

A variety of hydrophilic macromolecular monomers are available commercially. For example, commercially available monomers which have been found to be suitable are the 2-(2-ethoxyethoxy)ethyl acrylate which is available under the trade designation "SR-256" from Sartomer Company, West Chester, Pa.; the methoxy poly(ethylene oxide) acrylate which is available under the trade designation "No. 8816" from Monomer-Polymer & Dajac Laboratories, Inc., Trevose, Pa.; the methoxy poly(ethylene oxide) methacrylates of 200 Daltons, 400 Daltons, and 1000 Daltons which are available under the trade designations "No. 16664", "No. 16665" and "No. 16666", respectively, from Polysciences, Inc., Warrington, Pa.; and the hydroxy poly(ethylene oxide) methacrylate which is available under the trade designation "No. 16712" from Polysciences, Inc., Warrington, Pa.

Other preferred hydrophilic macromolecular monomers may be prepared using commercially available starting materials and conventional methods, for example, as described in U.S. Pat. No. 4,871,812 (Lucast).

In general, the hydrophilic macromolecular monomer is present in an amount of about 5 to 30% of the total weight of all monomers in the terpolymer. Preferred amounts for the monomers are about 10 to 20% by weight based upon the total amount of all monomers in the terpolymer.

Preferred polymers included in the PSA are (meth)acrylate polymers. Particularly useful adhesive compositions include a 65:15:20 2-ethylhexylacrylate:acrylic acid:copolymer blended with a nonreactive polyakylene oxide copolymer under the trade designation PLURONIC. Other suitable examples include a 90:10 iso-octyl acrylate:acrylic acid copolymer, a 70:15:15 isooctyl acrylate:ethyleneoxide acrylate:acrylic acid terpolymer, and a 25:69:6 2-ethylhexylacrylate:butyl acrylate:acrylic acid terpolymer. Useful adhesives can be any of those that are compatible with skin and useful for wound dressings, such as those disclosed in U.S. Pat. No. Re. 24,906 (Ulrich), U.S. Pat. No. 5,849,325 (Heinecke et al.), and U.S. Pat. No. 4,871,812 (Lucast et. al.) (water-based and solvent-based adhesives); U.S. Pat. No. 4,833,179 (Young et al.) (hot-melt adhesives); U.S. Pat. No. 5,908,693 (Delgado et al.) (microsphere adhesives); U.S. Pat. Nos. 6,171,985 and 6,083,856 (both to Joseph et al.) (low trauma fibrous adhesives); and, U.S. Pat. No. 6,198,016 (Lucast et al.), U.S. Pat. No. 6,518,343 (Lucast et al.), and U.S. Pat. No. 6,441,082 (Gieselman) (wet-skin adhesives). Inclusion of medicaments or antimicrobial agents in the adhesive is also contemplated, as described in U.S. Pat. No. 4,310,509 (Berglund) and U.S. Pat. No. 4,323,557 (Rosso).

The preferred pressure sensitive adhesives described above preferably transmit moisture vapor at a rate greater to or equal to that of human skin. While such a characteristic can be achieved through the selection of an appropriate adhesive, it is also contemplated in the present disclosure that other methods of achieving a high relative rate of moisture vapor transmission may be used, such as pattern coating the adhesive on the backing, as described in U.S. Pat. No. 4,595,001 (Potter et al.).

In the preferred embodiments according to the present disclosure, the choice of adhesives is limited to those that are safe to use on human skin, and preferably to those that are of the class known as "hypoallergenic". The preferred acrylate copolymers are adhesives of this class.

A composite of flexible film layer 110 coated with pressure-sensitive adhesive layer 120 preferably has a moisture vapor transmission rate of at least 300 g/m²/24 hrs/37° C./100%-10% relative humidity ("RH"), more preferably at least 700 g/m²/24 hrs/37° C./100%-10% RH, and even more preferably at least 2000 g/m²/24 hrs/37° C./100%-10% RH using the inverted cup method as described in U.S. Pat. No. 4,595,001.

Flexible film layer 110, also referred to herein as a "backing" layer, typically includes a liquid impervious, moisture vapor permeable polymeric film, although it can include a variety of other materials, which are preferably used in combination with a liquid impervious, moisture vapor permeable polymeric film. The liquid impervious, moisture vapor permeable polymeric film is a conformable organic polymeric material that preferably retains its structural integrity in a moist environment. Herein, "conformable" films are those that conform to a surface, even upon movement of the surface, as with the surface of a body part. As such, when the flexible film layer is applied to an anatomical feature, it conforms to the surface even when the surface is moved. The preferred flexible film layer is also conformable to animal anatomical joints. When the joint is flexed and returned to its unflexed position, the flexible film layer stretches enough to accommodate the flexion of the joint, but is resilient enough to continue to conform to the joint when the joint is returned to its unflexed condition. A description of this characteristic of flexible film layers preferred for use in wound dressings of the present disclosure can be found, for example, in U.S. Pat. No. 5,088,483 (Heineke) and U.S. Pat. No. 5,160,315 (Heineke).

Suitable films have a composition and thickness that allow for the passage of moisture vapor through them. The film aids in the regulation of water vapor loss from the wound area beneath the dressing. The film also acts as a barrier to both bacteria and to liquid water or other liquids.

The moisture vapor permeable polymeric films for use as flexible film layers in the present disclosure can be of a wide range of thicknesses. Preferably, they are at least 10 micrometers thick, and more preferably at least 12 micrometers thick. Preferably, they are no greater than to 250 micrometers, and more preferably no greater than 75 micrometers thick. Furthermore, they can include one or more layers tailored to have the desired properties. These layers can be coextruded and/or bonded together with adhesive layers, for example, as long as the overall properties of the film and wound dressing article, as described herein, are met.

Moisture vapor transmission rate ("MVTR") properties of a wound dressing article are important to allow the wound under the wound dressing to heal in moist conditions without causing the skin surrounding the wound to become macerated, and to facilitate optimum wear time and ease of removal.

A dry MVTR (or upright MVTR) of wound dressings or various components thereof, including the flexible film layer, can be measured by ASTM E-96-80 (American Society of Testing Materials) at 40° C. and 20% relative humidity using an upright cup method. Wet MVTR (or inverted MVTR) can be measured by the same method except that the sample jars are inverted so the water is in direct contact with the test sample.

Preferably, suitable films for use in the flexible film layer of the present disclosure have differential moisture vapor transmission properties. Preferably, a suitable film has a dry MVTR that is less than the wet MVTR of the film. Preferably, suitable films have a dry MVTR of at least 300 g/m²/24 hours and a wet MVTR of at least 3000 g/m²/24 hours. Preferably, the film has a wet MVTR greater 10,000 g/m²/24 hours, and more preferably greater than 15,000 g/m²/24 hours. The films can be tested using the ASTM E-96-80 test method already mentioned.

Examples of suitable materials for the liquid-impervious, moisture-vapor permeable polymeric films of the flexible film layer include synthetic organic polymers including, but not limited to: polyurethanes commercially available from B.F. Goodrich, Cleveland, Ohio, under the trade designation ESTANE, including ESTANE 58237 and ESTANE 58245; polyetheramide block copolymers commercially available from Elf Atochem, Philadelphia, Pa., under the trade designation PEBAX, including PEBAX MV 1074; polyetherester block copolymers commercially available from DuPont, Wilmington, Del., under the trade designation HYTREL; and thermoplastic elastomers commercially available from DSM Engineering Plastics, Evansville, Ind., under the trade designation ARNITEL VT. The polymeric films can be made of one or more types of monomers (e.g., copolymers) or mixtures (e.g., blends) of polymers. Preferred materials are thermoplastic polymers, e.g., polymers that soften when exposed to heat and return to their original condition when cooled. A particularly preferred material is a thermoplastic polyurethane.

Flexible films of the wound dressing articles of the present disclosure can also include other breathable materials including, for example, nonwoven, woven, and knit webs, porous films (e.g., provided by perforations or microporous structure), foams, paper, or other known flexible films. A preferred flexible film includes a combination of a liquid-impervious, moisture-vapor permeable polymeric film and a moisture-vapor permeable nonwoven web that can, among other advantages, impart enhanced structural integrity and improved aesthetics to the dressings. These layers of film and web may or may not be coextensive. A preferred such nonwoven web is a melt processed polyurethane (such as that available under the trade designation MORTHANE PS-440 from Morton International, Seabrook, N.H.), or hydroentangled nonwoven polyester or rayon-polyester webs (such as those available under the trade designation SONTARA 8010 or SONTARA 8411 from DuPont, Wilmington, Del.).

A composite of flexible film layer 110 coated with pressure-sensitive adhesive layer 120 (and any other intervening layers) preferably has a moisture vapor transmission rate of at least 300 g/m²/24 hrs/37° C./100%-10% relative humidity ("RH"), more preferably at least 700 g/m²/24 hrs/37° C./100%-10% RH, and even more preferably at least 2000 g/m²/24 hrs/37° C./100%-10% RH using the inverted cup method as described in U.S. Pat. No. 4,595,001.

In some embodiments, flexible film layer 110 is translucent, semi-transparent, or transparent, although this is not a requirement. Some examples of wound dressings that include a transparent or translucent flexible film layer are available under the trade designation TEGADERM, available from 3M Co., St. Paul, Minn.

A low adhesion coating (low adhesion backsize or LAB) can be provided on the flexible film layer on the side that may come into contact with an optional support layer. The low adhesion coating reduces the need to change the dressing due to unwanted dressing removal when other tapes or devices are placed on the dressing and removed, and reduces the surface friction of the dressing on linen or other fabrics, thereby offering additional protection against the accidental removal of dressing. A description of a low adhesion coating material suitable for use with a wound dressing article of the present disclosure can be found in U.S. Pat. No. 5,531,855 (Heineke) and U.S. Pat. No. 6,264,976 (Heineke).

In some embodiments, a wound dressing article of the present disclosure can include an absorbent layer disposed between the flexible film layer and the pressure-sensitive adhesive layer (i.e., the absorbent layer is an intervening layer disposed between the flexible film layer and the pressure-sensitive adhesive layer). Inclusion of a suitable absorbent layer can be advantageous, for example, when applying the wound dressing to wounds to accumulate exudates at the wound site.

Figure 2:
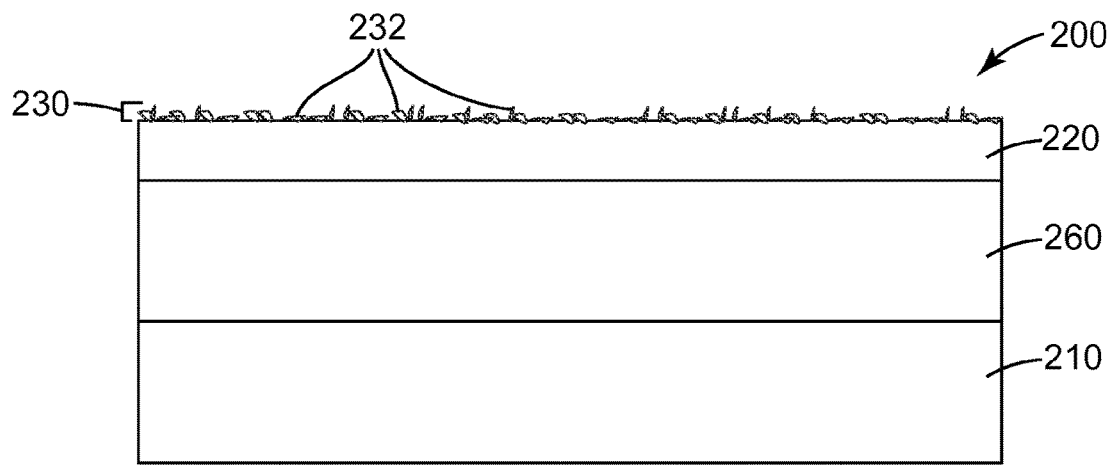
FIG. 2 is a schematic cross-section of an exemplary embodiment of a wound dressing article according to the present disclosure.

FIG. 2 illustrates an exemplary embodiment of a wound dressing article 200 of the present disclosure, including a flexible film layer 210, a pressure-sensitive adhesive layer 220 disposed on an absorbent layer 260, absorbent layer 260 disposed on flexible film layer 210, and a fibrin powder layer 230 disposed on a surface of pressure-sensitive adhesive layer 220 opposite flexible film layer 210. Fibrin powder layer 230 includes fibrin powder particles 232. Absorbent layer 260 is seen to be an intervening layer, disposed between pressure-sensitive adhesive layer 220 and flexible film layer 210. Pressure sensitive layer 220 may extend into and through a portion of absorbent layer 260, although this is not a requirement. Absorbent layer 260 can be adhered to flexible film layer 210 by a suitable adhesive layer (e.g., a pressure-sensitive adhesive layer).

In some embodiments, the absorbent layer can include an absorbent foam layer, or at least a portion of an absorbent foam layer disposed on the flexible film layer. A suitable foam layer can include, for example, an open cell foam selected from among the open cell foams described in U.S. Pat. No. 6,548,727 (Swenson). Suitable open cell foams preferably have an average cell size (typically, the longest dimension of a cell, such as the diameter) of at least about 30 microns, more preferably at least about 50 microns, and preferably no greater than about 800 microns, more preferably no greater than about 500 microns, as measured by scanning electron microscopy (SEM) or light microscopy. Such open cell foams when used in wound dressings of the present disclosure allow transport of fluid and cellular debris into and within the foam. Preferably, the foam includes a synthetic polymer that is adapted to form a conformable open cell foam that absorbs wound exudate. Examples of suitable materials for the absorbent, substantially non-swellable foams include synthetic organic polymers including, but not limited to: polyurethanes, carboxylated butadiene-styrene rubbers, polyesters, and polyacrylates. The polymeric foams can be made of one or more types of monomers (e.g., copolymers) or mixtures (e.g., blends) of polymers. Preferred foam materials are polyurethanes. A particularly preferred foam is a polyurethane, available under the trade designation POLYCRIL 400 from Fulflex, Inc., Middleton, R.I.

Figure 3:
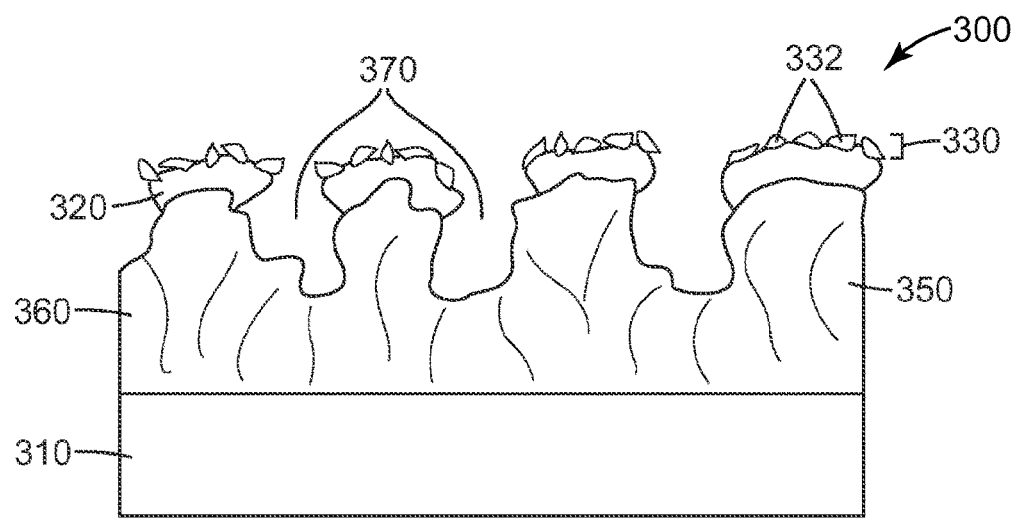
FIG. 3 is a schematic cross-section of an exemplary embodiment of a wound dressing article according to the present disclosure.

FIG. 3 illustrates an exemplary embodiment of a wound dressing article 300, including a flexible film layer 310, a pressure-sensitive adhesive layer 320 disposed on an absorbent layer 360, absorbent layer 360 disposed flexible film layer 310, and a fibrin powder layer 330 disposed on a surface of pressure-sensitive adhesive layer 320 opposite flexible film layer 310. Fibrin powder layer 330 includes fibrin powder particles 332. Absorbent layer 360 is seen to be an intervening layer, disposed between pressure-sensitive adhesive layer 320 and flexible film layer 310. In FIG. 3, Absorbent layer 360 is an open cell foam, having "cell wall" portions 350 defining "open cells" 370. Although not shown, it will be understood that open cells 370 extend throughout absorbent layer 360. As shown in FIG. 3, pressure sensitive adhesive layer 320 may be provided in a discontinuous form, at external surfaces of absorbent layer 360, to allow penetration of wound fluids and cellular debris into the absorbent foam layer. The fibrin particles 332 in fibrin powder layer 330 are thus displayed in correspondingly discontinuous manner at the outer surface of absorbent layer 360. Pressure-sensitive adhesive layer 320 may extend into and through a portion of absorbent layer 360, although this is not a requirement. Portions of pressure-sensitive adhesive layer 320 can extend over open cells 370, although it is desirable at least a portion (e.g., at least 10%, or at least 50%) of the cells at the external surface of absorbent layer 360 are not closed with PSA. Absorbent layer 360 can be adhered to flexible film layer 310 by a suitable adhesive layer (e.g., a pressure-sensitive adhesive layer).

In an embodiment of a method of the present disclosure, a solution of pressure-sensitive adhesive can be sprayed onto an open cell foam at a suitable coating weight (e.g., 5-15 mg/cm²) and after drying the PSA layer, a fibrin powder can be coated onto the adhesive coated surface. The fibrin particles can thus be deposited on an exterior surface of the foam (with some additional loading into pores of the open cell foam, as has been observed by SEM). Such a fibrin powder/PSA/absorbent foam construct has been observed to readily absorb moisture.

In another embodiment (not shown), the absorbent layer may comprise a non-woven or a fiber material. In an embodiment where the absorbent material includes a fiber material, the fiber material can be a sheath-core fiber having a central core of absorbent fiber and a sheath comprising pressure-sensitive adhesive.

In some embodiments, the absorbent layer may extend around a peripheral region of the wound dressing, in to absorb fluids that might otherwise accumulate on skin and result in undesirable skin degradation (e.g., maceration). In such embodiments, an absorbent layer would not need to be included in a more central region of the wound dressing (e.g., the portion of the wound dressing that is in contact with the wound, or positioned over the wound).

In another embodiment (not shown), a fibrin powder layer can be disposed on a pressure-sensitive adhesive layer, which in turn is disposed on a flexible, porous, non-woven backing layer. The non-woven backing layer can be reinforced with filaments (e.g., polyester filaments) for added strength. An example of such a non-woven-backing coated with a (hypoallergenic) pressure-sensitive adhesive can include sterile skin closure strips (e.g., STERI-STRIPS, available from 3M Co., St. Paul, Minn.). The addition of a fibrin powder layer to such sterile skin closure strips can have beneficial effects, for example, in scar management at incision or wound sites (i.e., to reduce scar formation).

A wound dressing article of the present description can further include a release liner. The release liner can be disposed against the fibrin powder layer, and also make sufficient contact with the pressure-sensitive adhesive layer to at least partially adhere to the pressure-sensitive adhesive layer. Thus, the fibrin powder layer is disposed between the pressure-sensitive adhesive layer and the release liner. The release liner can be removed from the wound dressing article without significantly damaging the fibrin powder layer, for example, to allow for application of the fibrin powder layer to remain on the PSA layer and to be applied against the surface of a wound.

Methods of making a wound dressing article of the present disclosure can include distributing a fibrin powder onto a pressure-sensitive adhesive layer disposed on a flexible film layer. Alternatively, the fibrin powder can be suspended in a liquid (e.g., an inert, volatile fluorinated liquid) and spray dried in a dehydrated form onto the surface of a pressure-sensitive adhesive layer disposed on a flexible film layer. Examples of suitable wound dressings that include a pressure-sensitive adhesive layer disposed on flexible film layer include TEGADERM wound dressings (e.g., TEGADERM 1626) available from 3M Co., St. Paul, Minn. In a preferred embodiment, fibrin powder is applied to the surface of a pressure-sensitive adhesive layer of a TEGADERM wound dressing.

A wound dressing article of the present description is typically provided in a package format (i.e., positioned in a sealed package). The interior of the sealed package is typically sterile. Examples of wound dressing packages suitable for use with the wound dressings and methods of this disclosure include, for example, polymeric packages and foil packages. A wide variety of polymeric materials may be used to make non-porous packages suitable for use with the wound dressings. The packaging material may be, for example, polyethylene, polypropylene, copolymers of ethylene and propylene, polybutadiene, ethylene-vinyl acetate, ethylene-acrylic acid, or ionomeric films. Suitable foil packages can include aluminum foil packages. In some embodiments, the packaging material may be used as sheets of material which are placed above and below the wound dressing and then sealed on four sides to generate the package. In other embodiments, a pre-made pouch is utilized which has 3 sides already sealed. After the wound dressing article is placed within the pouch the fourth side is sealed to form the package. Sealing of the package can be achieved by heat sealing (i.e. by the application of heat and pressure to form a seal) or the use of adhesive sealants can be used to seal the packages (for example pressure sensitive adhesive sealants or cold seal sealants). Typically, heat sealing is used. Additionally, packaging systems can be used which include placing the wound dressing in a porous package that is then placed in a non-porous package, such as a foil package. The foil package prevents moisture loss prior to use and the porous package permits easy handling during use.

An advantage of a wound dressing article of the present disclosure is that it can be sterilized by a terminal sterilization process that includes exposure to ethylene oxide or, advantageously, gamma-irradiation. Once the fibrin powder layer has been applied at certain levels to a pressure-sensitive adhesive layer disposed on a flexible film layer, the dressing can be sterilized by application of gamma radiation. This irradiation can be carried out whether or not the wound dressing article is contained within a package. The exposure times and levels of radiation doses applied to the wound dressings to achieve sterilization can vary based upon a variety of factors, including the gamma equipment used as well as the inherent bioburden levels present in the wound dressing. Typically, to achieve sterilization of a wound dressing, a Sterility Assurance Level (SAL) of $10^{-6}$ is required. This SAL level is typically achieved by exposing the wound dressing to a minimum cumulative gamma irradiation dose. Depending on the bioburden levels in an unsterilized dressing and the size of the dressing, the minimum cumulative dose can range from about 10 kGy to about 35 kGy. Typically the minimum cumulative dose is about 15 to 30 kGy. The required gamma radiation dose to achieve sterility can be done in a single pass or multiple passes through the gamma irradiation sterilizer. For example, exposing the wound dressing to 5 sterilization cycles using a dose of 5 kGy per cycle would be similar to exposing the wound dressing to one dose of 25 kGy of gamma irradiation. Due to labor and time constraints, it is generally desirable to minimize the number of passes that a wound dressing experiences through the gamma irradiation sterilizer. Typically, it is desirable that the number of passes through the sterilizer be five or less, and it may be even more desirable for the number of passes to be two or less. Exposure time may be viewed as the time a sample to be sterilized is exposed to the gamma radiation. Typically the exposure time is on the order of hours.

Gamma radiation is a suitable method to sterilize the wound dressings of this disclosure. Exposure of the wound dressings of this disclosure to a suitable level gamma irradiation does not produce a comparable loss of re-epithelialization performance.

The ability to use terminal sterilization can provide an advantage over other forms of wound dressings that include, for example, a liquid. Without being bound by theory, aqueous solutions or suspensions of proteins such as fibrinogen and thrombin can be expected to undergo inter-chain crosslinking during terminal sterilization that involves gamma-irradiation. In a dry format, a protein will often undergo chain scission (i.e., degradation) and thereby lose enzymatic activity. Thus, gamma-irradiation of the reagents for a polymerization (e.g., fibrinogen and/or thrombin) may result in crosslinking and/or chain scission of the separate reagents, and thus no reaction (or no polymerization) to form fibrin. Depending on the level of gamma-irradiation, fibrin may also undergo some chain scission, although even with low levels of degradation, the gamma-irradiated fibrin still can be recognized by cells to obtain the desired re-epithelialization effect.

SELECT EMBODIMENTS OF THE PRESENT DISCLOSURE

Various embodiments are provided that include a wound dressing, a method of making a wound dressing, and a method of using a wound dressing.

Embodiment 1

A wound dressing article comprising:
a flexible film layer;
a pressure-sensitive adhesive layer disposed on the flexible film layer; and
a fibrin powder layer disposed on a surface of the pressure-sensitive adhesive layer opposite the flexible film layer.

Embodiment 2

The article of embodiment 1, wherein the fibrin powder comprises fibrin powder particles in the form of microspheres, amorphous particles, or a mixture thereof.

Embodiment 3

The article of embodiment 2, wherein the fibrin powder particles have an average particle size in largest dimension of up to 100 micrometers.

Embodiment 4

The article of any one of the preceding embodiments, wherein a coating weight of the fibrin powder layer is in a range from 0.2 to 20 milligrams per $cm^2$

Embodiment 5

The article of any one of the preceding embodiments, wherein the fibrin powder layer contains fibrin in a range of 1 to 99 percent by weight, relative to a total weight of the fibrin powder layer.

Embodiment 6

The article of any one of the preceding embodiments, wherein the surface of the flexible film layer having the pressure-sensitive adhesive layer disposed thereon comprises a microstructured surface.

Embodiment 7

The article of any one of the preceding embodiments, further comprising an absorbent layer disposed between the flexible film layer and the pressure-sensitive adhesive layer.

Embodiment 8

The article of embodiment 7, wherein the absorbent layer is an open cell foam.

Embodiment 9

The article of embodiment 8, wherein the pressure-sensitive adhesive layer is discontinuous.

Embodiment 10

The article of embodiment 7, wherein the absorbent layer comprises a nonwoven or a fiber material.

Embodiment 11

The article of embodiment 10, wherein the fiber material comprises sheath-core fiber having a central core of absorbent fiber and a sheath comprising pressure-sensitive adhesive.

Embodiment 12

The article of any one of the preceding embodiments, further comprising a release liner, wherein fibrin powder layer is disposed between the pressure-sensitive adhesive layer and the release liner.

Embodiment 13

The article of any one of the preceding embodiments, wherein the flexible film layer is substantially transparent.

Embodiment 14

The article of any one of the preceding embodiments, wherein the fibrin powder layer comprise at least one additive.

Embodiment 15

An article comprising the wound dressing article of any one of embodiments 1 to 14 positioned in a sealed packaged.

Embodiment 16

The article of embodiment 15, wherein the sealed package comprises a sterile interior.

Embodiment 17

A method of making a wound dressing article, the method comprising:
providing a flexible film layer;
disposing a pressure-sensitive adhesive layer on the flexible film layer;
forming a fibrin powder layer on a surface of the pressure-sensitive adhesive layer opposite the flexible film layer to prepare the wound dressing article.

Embodiment 18

The method of embodiment 17, wherein providing the fibrin powder comprises drying a fibrin-containing gel to form a dried fibrin-containing composition, and crushing the dried fibrin-containing composition to form the fibrin powder.

Embodiment 19

The method of any one of embodiments 16 to 17, further comprising subjecting the wound dressing article to terminal sterilization, wherein the terminal sterilization comprises gamma irradiation.

Embodiment 20

A method of treating a wound, comprising applying a wound dressing article according to any one of embodiments 1 to 14 to an external wound on a mammal.

Embodiment 21

The method of embodiment 20, wherein the mammal is a human.

EXAMPLES

Unless otherwise noted, all parts, percentages, ratios, etc. in the Examples and the rest of the specification are by weight. "Weight percent" is in some places abbreviated as "wt. %".

Materials

HEPES, $CaCl_2$, NaCl were obtained from Sigma-Aldrich (Milwaukee, Wis.). Other materials are listed in Table 1.

TABLE 1

| Material | Description |
| --- | --- |
| EPILIFE medium | Growth media supplemented with an HKGS kit, obtained from Invitrogen, Grand Island, NY (Catalog No. S-001-5) |
| Fibrinogen | Fibrinogen from bovine plasma was obtained from Sigma-Aldrich, Milwaukee, WI, catalog number F8630 |
| HDFa | Adult human dermal fibroblasts, obtained from Invitrogen, Grand Island, NY (Catalog No. C-013-5C) |
| HEKa | Adult human epidermal keratinocytes, obtained from Invitrogen, Grand Island, NY (Catalog No. C-005-5C) |
| TEGADERM 1626 | Wound dressing article including a PSA layer, obtained from 3M Company, Saint Paul, MN, under the trade designation "TEGADERM 1626" |
| Thrombin | Thrombin from bovine plasma was obtained from Sigma-Aldrich, Milwaukee, WI, catalog number T6634 |

Illustrative Example

Migration of Human Epidermal Keratinocytes Under a Fibrin Gel

Adult human epidermal keratinocytes (HEKa) were expanded in culture to the end of passage 2 using "EPILIFE" medium supplemented with an HKGS kit according to manufacturer's instructions. Cells were then further expanded for experimental use. At the end of passage 3, the HEKa cells were stained with CELLTRACKER GREEN (obtained from Invitrogen, Catalog No. C2925), trypsinized, and then concentrated via centrifugation to give a HEKa cell suspension having a concentration of $10 \times 10^6$ cells/mL. A 5 microliter drop of this HEKa cell suspension was plated in the center of each well of a 24-well plate and allowed to incubate at 37° C. for 15 minutes. After 15 minutes, the incubated HEKa cells were then covered either with (a) 1 mL of the EPILIFE medium, or with (b) 1 mL of a 4.5 mg/mL solution of an in situ polymerized fibrin gel. The solution for in situ polymerization of a fibrin gel was formed by mixing 1 mL of a 30 mg/mL fibrinogen solution with 5 mL of 20 mM HEPES in saline (0.9 wt. % NaCl in water), 81 microliters of 2M $CaCl_2$ and 67.5 microliters of 25 IU/mL thrombin. Composition of solids in the polymerized fibrin gels was calculated to give the following percentages (by weight):

| | | |
| --- | --- | --- |
| Fibrin | 4.5 mg | (23.9 wt. %) |
| HEPES | 3.93 mg | (20.9 wt. %) |
| NaCl | 7.43 mg | (39.4 wt. %) |
| $CaCl_2$ | 3.00 mg | (15.9 wt. %) |
| Thrombin | 0.281 IU = 237 ng | (<0.01 wt. %) |

A coating weight of fibrin in the polymerized fibrin gel was calculated to be approximately 2 $mg/cm^2$.

After fibrin polymerization (about 30 minutes), the polymerized fibrin gel overcoating the HEKa had an additional 1 mL EPILIFE placed on top. The 24-well plate was then immediately imaged using an inverted fluorescence microscope (obtained from Leica Microsystems, Buffalo Grove, Ill., under the trade designation "LEICA DMI6000B") using a green-fluorescent protein (GFP Ex/Em (490/530)) and an automated, mechanical stage with Mark and Find capabilities (the Mark and Find capabilities allowed monitoring of a single position within the plate even with removal of the plate from the stage for incubation). While there was essentially no migration evident for the HEKa cells treated with growth medium only, the HEKa cells treated with fibrin gels were observed to migrate up to about 300 micrometers after 48 hours.

Example 1

Migration of HEKa Cells in a Human Skin Equivalent In Vitro Model

Based on the results of Illustrative Example 1, a prototype device was developed that could deliver fibrin to model wound in vitro. A human skin equivalent ("HSE") article was utilized for the model system (see, for example, Boyce, "Design principles for composition and performance of cultured skin substitutes", Burns, (27) 2001; Supp et al., "Engineered skin substitutes: practices and potentials", Clinics Dermatol., (23) 2005; and Barai et al., "Improvements of Epidermal Barrier Properties in Cultured Skin Substitutes after Grafting onto Athymic Mice", Skin Pharmacology Physiology, (20) 2007). HSE articles were fabricated by incorporating adult human dermal fibroblasts (HDFa) into a collagen gel followed by subsequent co-culture with HEKa cells. Patterned seeding of the HEKa cells onto the top layer of the HSE resulted in an epithelial "wound" that could be treated with the prototype device. An overall diameter of the HSE was 30 mm, with an open "wound" area central to the HSE, the open area having a diameter of 13 mm. The HSE was placed in 10% neutral buffered formalin to halt cell growth at selected time points (3, 7, or 14 days) after the placement of the varying treatment groups and evaluated histologically.

In this example, wound dressing included fibrin powder layer coated onto the PSA side of a TEGADERM 1626 wound dressing having a PSA layer. The wound dressing was made by first forming a fibrin gel as described in the Illustrative Example and then lyophilizing the fibrin gel to leave a dried fibrin-containing material. The dried fibrin-containing material remaining after lyophilization was then crushed into a powder and spread across the adhesive surface, giving a wound dressing having a fibrin powder layer. It was determined (by weighing) that 150 mg of powder was adhered to the adhesive surface of the wound dressing, resulting in a coating weight of 2 mg/cm$^2$.

Figure 4:
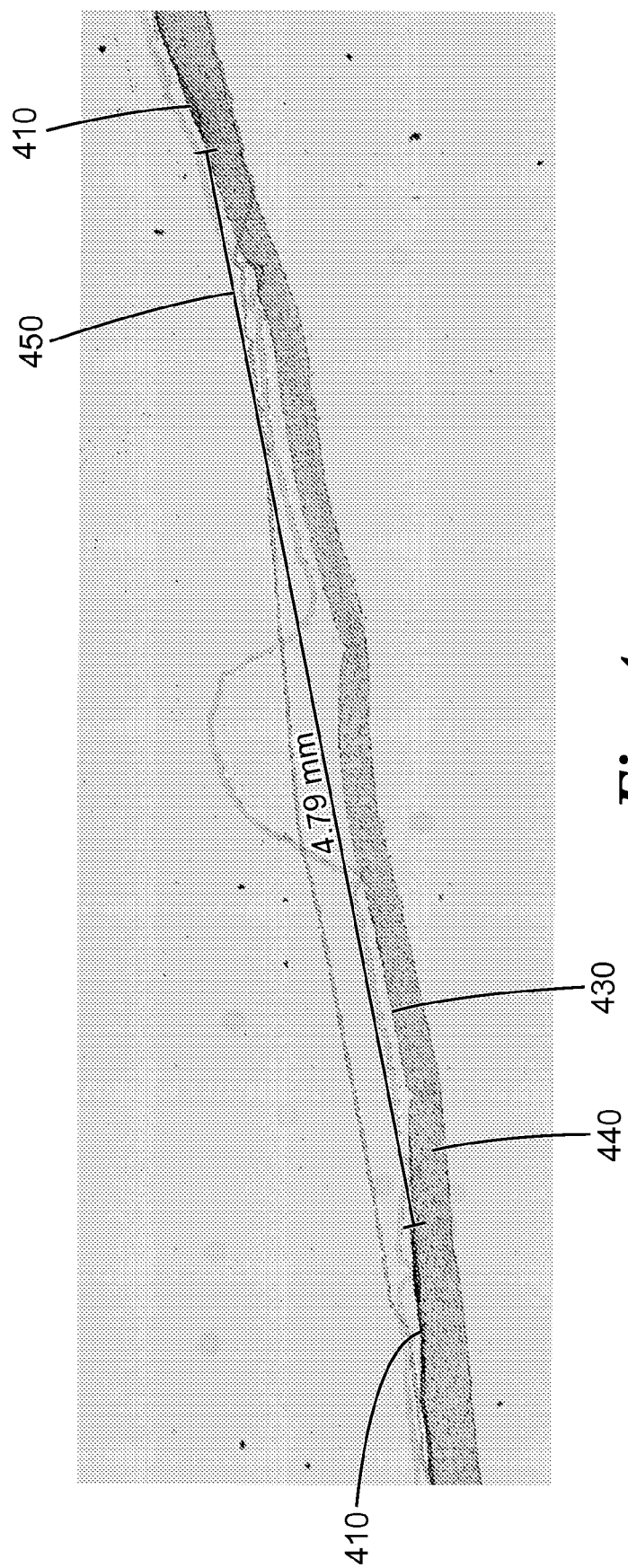
FIG. 4 is a light microscopy image of a control wound sample according to the present disclosure.
Figure 5:
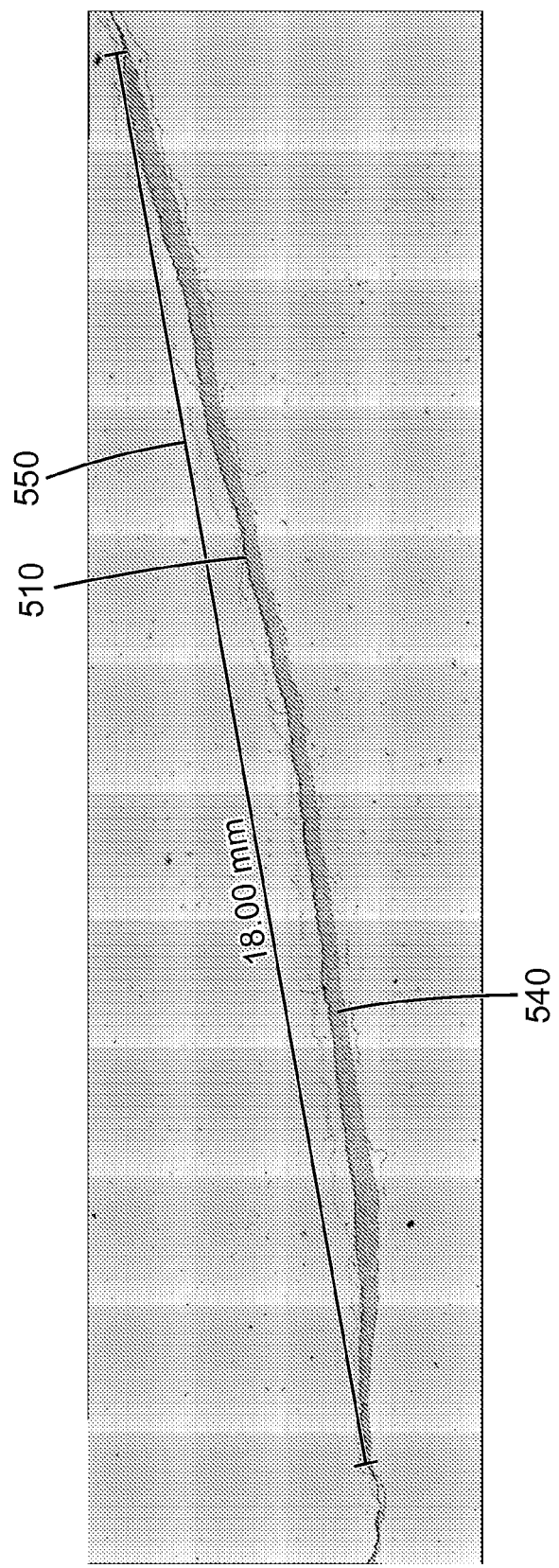
FIG. 5 is a light microscopy image of a fibrin-treated wound sample according to the present disclosure.

From the above fibrin-coated wound dressing, 20 mm disks were die-punched and placed onto the "epidermal" surface of the HSE devices 540, centralized over the open "wound" area. As a control, 20 mm disks from a non-coated TEGADERM 1626 dressing were placed on to the epidermal surface 430 of additional samples 440. The HSEs were sampled at 3, 7, and 14 days post-treatment to histologically evaluate the migration of HEKa cells across the open dermal surface. Representative standard light microscopy images of the samples harvested after 7 days are shown in FIG. 4 (non-fibrin treated) and in FIG. 5 (fibrin-treated). Samples treated with the non-coated wound dressing (i.e., not having a fibrin coating) exhibited partial wound closure at 7 days (see FIG. 4; "epithelial" layer 410 exhibited partial re-epithelialization, but wound length 450 (4.79 mm) had not been re-epithelialized by day 7) and full wound closure at 14 days (not shown), while the fibrin-coated wound dressings exhibited partial wound closure at 3 days (not shown) and full wound closure at 7 days (see FIG. 5, epithelial layer 510 had grown completely across wound length 550 (the 18 mm length included the original 13 mm wound) by day 7 to form re-epithelialized layer 530), which demonstrated enhancement of wound re-epithelialization by including a fibrin coating on the wound dressing.

Illustrative Example 2

Migration of HEKa Cells Under a Fibrin Film Flood-Coated onto TEGADERM 1626

A similar experiment was conducted as described in Example 1, except the solution for in situ polymerization of a fibrin gel was flood coated onto the adhesive surface of a TEGADERM 1626 wound dressing and then allowed to dry overnight at room temperature. After drying, 20 mm punches were made and these placed on the epidermal surface of HSEs (an HSE is the "human skin equivalent" in the model system described in Example 1). The control treatment was a TEGADERM 1626 dressing without a fibrin coating. The HSEs were sampled at 3, 7, and 14 days post-treatment to histologically evaluate the migration of HEKa across the open dermal surface. The results (not shown) of this experiment were similar to those observed in Example 1: samples treated with fibrin-coated TEGADERM 1626 dressing demonstrated faster epidermal closure than samples treated with the TEGADERM 1626 dressing lacking the fibrin coating.

Fibrin Powder/PSA/Absorbent Foam Article

Figure 6:
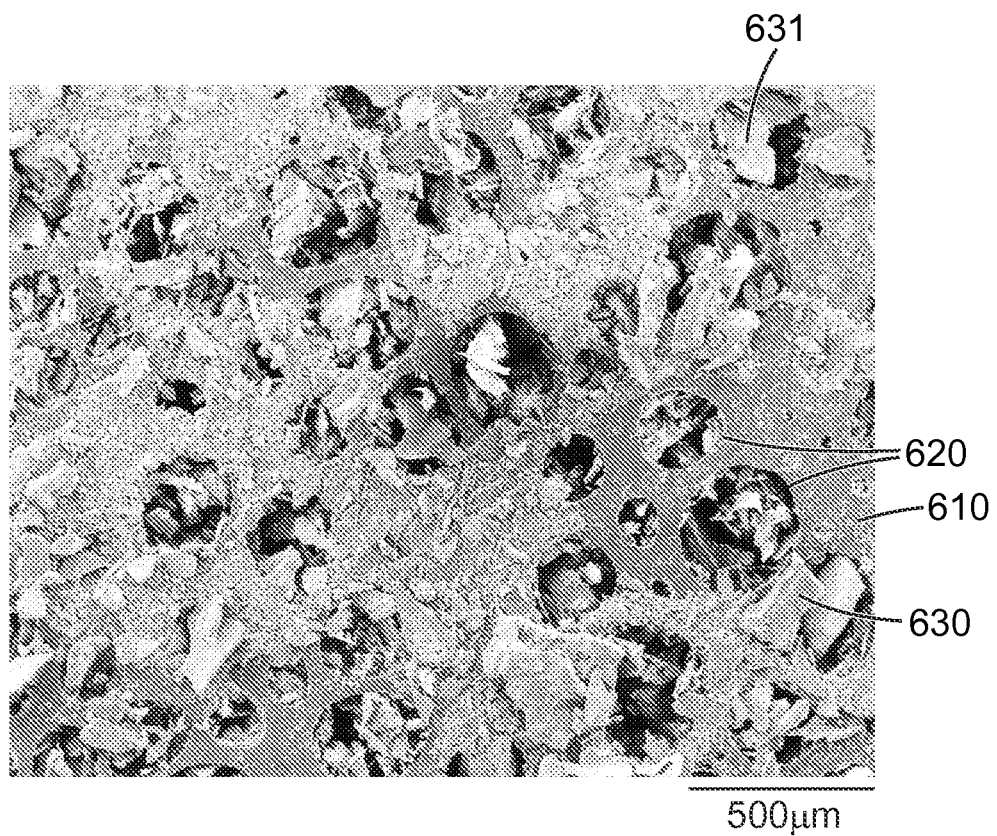
FIG. 6 is a digital image obtained by scanning electron microscopy of an absorbent foam coated with a pressure-sensitive adhesive and a layer of fibrin powder.

A pressure sensitive adhesive solution (isooctyl acrylate and acrylamide combined in a 97:3 weight ratio and dissolved at 33 wt. % solids in a solvent mixture of 51 wt. % heptanes and 49 wt. % EtOAc) was diluted 1:1 by volume in pentane. This solution was then put into an aerosolization jar, and then was sprayed onto a layer of an absorbent foam (obtained from 3M Co., St. Paul, Minn., under the trade designation "3M 90600 TEGADERM FOAM DRESSING (NONADHESIVE)"), followed by drying at 50° C. for 10 minutes, to provide an adhesive coating weight of 11.5 mg/cm$^2$ on the absorbent foam. Fibrin powder (prepared as in Example 1) was coated onto the resulting adhesive coated surface with a fibrin powder coating weight of 3.7 mg/cm$^2$. The resulting absorbent foam coated with PSA and fibrin powder was found to readily absorb moisture. FIG. 6 is a digital image obtained by scanning electron microscopy of the coated absorbent foam, which showed fibrin powder particles 630 distributed on the surface 610 of the layer of absorbent foam, with additional loading of fibrin powder particles 631 into the pores 620 of the foam.

Other modifications and variations to the present disclosure may be practiced by those of ordinary skill in the art, without departing from the spirit and scope of the present disclosure. It is understood that aspects of the various embodiments may be interchanged in whole or part or combined with other aspects of the various embodiments. The preceding description, given in order to enable one of ordinary skill in the art to practice the claimed disclosure, is not to be construed as limiting the scope of the disclosure, which is defined by the claims and all equivalents thereto.

What is claimed is:

1. A wound dressing article comprising:
   a flexible film layer;
   a pressure-sensitive adhesive layer disposed on the flexible film layer;
   an absorbent layer disposed between the flexible film layer and the pressure-sensitive adhesive layer; and
   a fibrin powder layer disposed on a surface of the pressure-sensitive adhesive layer opposite the flexible film layer;
   the pressure sensitive adhesive layer extends into and through a portion of absorbent layer.

2. The article of claim 1, wherein the fibrin powder comprises fibrin powder particles in the form of microspheres, amorphous particles, or a mixture thereof.

3. The article of claim 2, wherein the fibrin powder particles have an average particle size in largest dimension of up to 100 micrometers.

4. The article of claim 1, wherein a coating weight of the fibrin powder layer is in a range from 0.2 to 20 milligrams per cm$^2$.

5. The article of claim 1, wherein the fibrin powder layer contains fibrin in a range of 1 to 99 percent by weight, relative to a total weight of the fibrin powder layer.

6. The article of claim 1, wherein the surface of the flexible film layer having the pressure-sensitive adhesive layer disposed thereon comprises a microstructured surface.

7. The article of claim 1, wherein the pressure-sensitive adhesive layer is discontinuous.

8. The article of claim 1, wherein the absorbent layer comprises a nonwoven or a fiber material.

9. The article of claim 8, wherein the fiber material comprises sheath-core fiber having a central core of absorbent fiber and a sheath comprising pressure-sensitive adhesive.

10. The article of claim 1, further comprising a release liner, wherein the fibrin powder layer is disposed between the pressure-sensitive adhesive layer and the release liner.

11. The article of claim 1, wherein the flexible film layer is substantially transparent.

12. The article of claim 1, wherein the fibrin powder layer comprise at least one additive.

13. An article comprising the wound dressing article of claim 1 positioned in a sealed packaged.

14. The article of claim 13, wherein the sealed package comprises a sterile interior.

15. A method of making a wound dressing article, the method comprising:
   providing a flexible film layer;

disposing a pressure-sensitive adhesive layer on the flexible film layer;

disposing an absorbent layer between the flexible film layer and the pressure-sensitive adhesive layer;

forming a fibrin powder layer on a surface of the pressure-sensitive adhesive layer opposite the flexible film layer to prepare the wound dressing article;

wherein the absorbent layer is an open cell foam having open cells;

wherein the pressure sensitive adhesive layer extends into and through a portion of the absorbent layer.

16. The method of claim 15, wherein forming the fibrin powder comprises drying a fibrin-containing gel to form a dried fibrin-containing composition, and crushing the dried fibrin-containing composition to form the fibrin powder.

17. The method of claim 14, further comprising subjecting the wound dressing article to terminal sterilization, wherein the terminal sterilization comprises gamma irradiation.

18. A method of treating a wound, comprising applying a wound dressing article according to claim 1 to an external wound on a mammal.

19. The method of claim 18, wherein the mammal is a human.

20. The article of claim 1, wherein the absorbent layer is an open cell foam.

21. A wound dressing article comprising:
a flexible film layer;
a pressure-sensitive adhesive layer disposed on the flexible film layer;
an absorbent layer disposed between the flexible film layer and the pressure-sensitive adhesive layer; and
a fibrin powder layer disposed on a surface of the pressure-sensitive adhesive layer opposite the flexible film layer;
wherein the absorbent layer is an open cell foam having open cells;
wherein portions of the pressure-sensitive adhesive layer extends over the open cells.

* * * * *

UNITED STATES PATENT AND TRADEMARK OFFICE
CERTIFICATE OF CORRECTION

PATENT NO. : 10,772,767 B2  Page 1 of 1
APPLICATION NO. : 14/899608
DATED : September 15, 2020
INVENTOR(S) : Bjork et al.

It is certified that error appears in the above-identified patent and that said Letters Patent is hereby corrected as shown below:

On the Title Page

Column 2 (Other Publications)
Line 2, Delete "Athyic" and insert -- Athymic --, therefor.

In the Specification

Column 6
Line 65, Delete "Fibin" and insert -- Fibrin --, therefor.

Column 8
Line 7, Delete "FIG." and insert -- FIGS. --, therefor.

Column 10
Line 28, Delete "poly(l-alkene)" and insert -- poly(1-alkene) --, therefor.

Column 21
Line 45 (Approx.), Delete "cm²" and insert -- cm². --, therefor.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*